(12) United States Patent
Reiter et al.

(10) Patent No.: US 7,507,408 B2
(45) Date of Patent: *Mar. 24, 2009

(54) ANTI HEPATITIS C VIRUS ANTIBODY AND USES THEREOF

(75) Inventors: Christian Reiter, Karsfeld (DE); Francois Habersetzer, Illkirch-Graffenstaden (FR); Anne Fournillier, Lyons (FR); Christian Trepo, Bron (FR); Claude Desgranges, Paris (FR); Genevieve Inchauspe, Lyons (FR)

(73) Assignee: Genmab A/S, Copenhagen-K (DK)

( * ) Notice: Subject to any disclaimer, the term of this patent is extended or adjusted under 35 U.S.C. 154(b) by 342 days.

This patent is subject to a terminal disclaimer.

(21) Appl. No.: 10/972,296

(22) Filed: Oct. 25, 2004

(65) Prior Publication Data

US 2006/0153833 A1 Jul. 13, 2006

Related U.S. Application Data

(62) Division of application No. 09/744,176, filed on Jun. 18, 2001, now Pat. No. 6,951,646.

(30) Foreign Application Priority Data

Jul. 21, 1998 (EP) .................................. 98113595
Jul. 20, 1999 (EP) ...................... PCT/EP99/05173

(51) Int. Cl.
*A61K 39/29* (2006.01)
*A61K 39/42* (2006.01)
*A61K 39/12* (2006.01)
*C12Q 1/70* (2006.01)
*G01N 35/53* (2006.01)

(52) U.S. Cl. ............. 424/149.1; 424/141.1; 424/134.1; 424/135.1; 424/139.1; 424/142.1

(58) Field of Classification Search ............. 424/228.1, 424/130.1; 530/338.1, 338.3
See application file for complete search history.

(56) References Cited

U.S. PATENT DOCUMENTS 6,150,134 A 11/2000 Maertens et al.
6,682,909 B2 1/2004 Nakano et al.
6,692,908 B1 2/2004 Foung et al.

FOREIGN PATENT DOCUMENTS

DE 0520499 A1 12/1992
WO WO 9740176 10/1997

OTHER PUBLICATIONS

Rosa et al., *A Quantitative Test to Estimate Neutralizing Antibodies to the Hepatitis C Virus: Cytofluorimetric Assessment of Envelope Glycoprotein 2 Binding to Target Cells.* Proc. Natl. Acad. Sci. (1996), vol. 93, pp. 1759-1763.
Antonella Cerino, *Antibody Responses to the Hepatitis C Virus E2 Protein: Relationship to Viraemia and Prevalence in Anti-HCV Seronegative Subjects.* Journal of Medical Virology (1997), 51:1-5.
Rajen Koshy and Genevieve Inchauspe, *Evaluation of Hepatitis C Virus Protein Epitopes for Vaccine Development.* Tibtech (1996), vol. 14, pp. 364-369.
Habersetzer et al., *Characterization of Human Monoclonal Antibodies Specific to the Hepatitis C Virus Glycoprotein E2 with In Vitro Binding Neutralization Properties.* Virology (1998), 249:32-41.
Habersetzer et al., *Isolation of Human Monoclonal Antibodies (HMAb₃) Directed at Conformational Determinants of the Hepatitis C Virus (HCV) E2 Envelope Protein.* Hepatology (1996), vol. 24, No. 4, Pt. 2, p. 381A.
Lee et al., *Identification of a Domain Containing B-Cell Epitopes in Hepatitis C Virus E2 Glycoprotein by Using Mouse Monoclonal Antibodies.* Journal of Virology (1999), vol. 73, No. 1, pp. 11-18.
Deleersnyder et al., *Formation of Native Hepatitis C Virus Glycoprotein Complexes.* Journal of Virology (1997), vol. 71, No. 1, pp. 697-704.
Nakano et al., J. Virol. 1997, vol. 71, pp. 7101-7109.
Fields Virology edited by Fields et al. 1995, vol. 1, lines 1-60 on right col., p. 1039.
Okamato, Virology 1992, vol. 188, pp. 331-341.
Bending et al., Methods: A companion to Methods in Enzymology 1995, vol. 8, pp. 83-93.
Rudikoff et al., Proc. Natl. Acad. Sci. USA 1982, vol. 79, p. 1979.
Cardoso et al., J. Medi. Virol. 1998, vol. 55, pp. 28-34.
Burioni et al., Hepatology 1998, vol. 28, pp. 810-814.

*Primary Examiner*—Bruce Campell
*Assistant Examiner*—Bao Qun Li
(74) *Attorney, Agent, or Firm*—Bell, Boyd & Lloyd LLP

(57) ABSTRACT

Described are novel antibodies specifically recognizing conformation dependent epitopes of HCV glycoprotein E2 and that are capable aof neutralizing the binding of E2 protein onto susceptible cells. Furthermore, antigens and epitopes recognized by the above-described antibodies as well as polynucleotides encoding said antibodies are provided. Also provided are to vectors comprising said polynucleotides as well as host cells transformed therewith and their use in the production of said antibodies. In addition, pharmaceutical and diagnostic compositions are provided comprising any of the aforedescribed antibodies, antigens, epitopes, polynucleotides, vectors or cells. Further described is the use of the aforementioned antibodies, antigens, polynucleotides and vectors in adoptive immunotherapy, preferably for the treatment or prevention of HCV infection during liver transplantation.

5 Claims, 7 Drawing Sheets

Figure 1:
Figure 1:
Figure 1:
Figure 1:
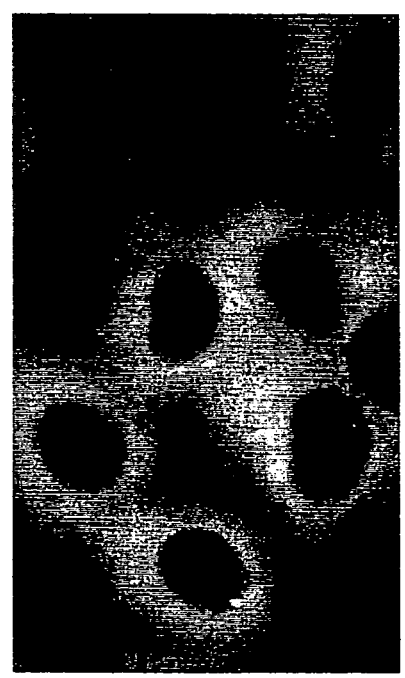
Figure 1:
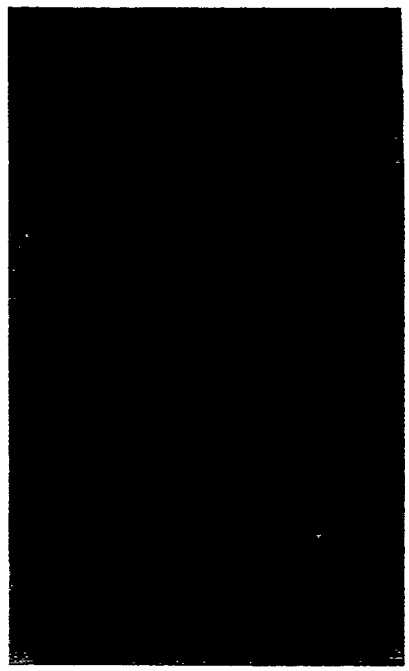
Figure 1:
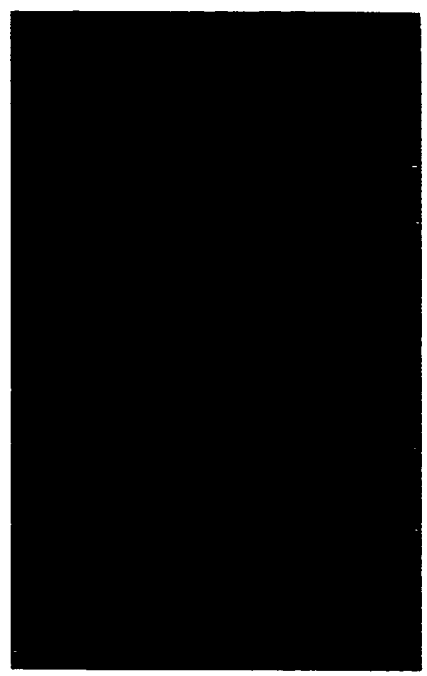

E
F

■ 503
▲ 108

% Neutralization of E2 binding vs. Concentration of HumAbs (µg/ml)

Figure 4

```
                9                18                27                36                45                54
5' TCT TAC GAG CTC ACG CAG CCG CCC TCG GTG TCA GTG TCC CCA GGA CAG ACG GCC
    S   Y   E   L   T   Q   P   P   S   V   S   V   S   P   G   Q   T   A 63                72                81                90                99               108
   AGG ATC ACC TGC TCT GGA GAT GCA TTG CCA AAG CAA TAT GCT TAC TGG TAT CAG
    R   I   T   C   S   G   D   A   L   P   K   Q   Y   A   Y   W   Y   Q 117               126               135               144               153               162
   CAG AAG CCA GGC CAG GCC CCT GTG TTG GTG ATA TAT AAA GAT AAT GAG AGG CCC
    Q   K   P   G   Q   A   P   V   L   V   I   Y   K   D   N   E   R   P 171               180               189               198               207               216
   TCA GGG ATC CCT GAG CGA TTC TCT GGC TCC AGG TCA GGG ACA ACA GTC ACG TTG
    S   G   I   P   E   R   F   S   G   S   R   S   G   T   T   V   T   L 225               234               243               252               261               270
   ACC ATC AGT GGA GTC CAG GCA GAA GAC GAG GCT GAC TAT TAC TGT CAA TCA GCA
    T   I   S   G   V   Q   A   E   D   E   A   D   Y   Y   C   Q   S   A 279               288               297               306               315               324
   GAC AGC AGT GGT TCT TCC TGG GTG TTC GGC GGA GGG ACC AAG CTG ACC GTC CTA
    D   S   S   G   S   S   W   V   F   G   G   G   T   K   L   T   V   L
3'
```

Figure 5

```
                 9                  18                 27                 36                 45                 54
5' CAG GTG CAG CTA CAG CAG TGG GGC GCA GGA CTG TTG AAG CCT TCG GAG ACC CTG
   --- --- --- --- --- --- --- --- --- --- --- --- --- --- --- --- --- ---
    Q   V   Q   L   Q   Q   W   G   A   G   L   L   K   P   S   E   T   L 63                 72                 81                 90                 99                108
   TCC CTC ACC TGC GCT GTC TAT GGT GGG TCC TTA AGT GGT TAC TTC TGG ACC TGG
   --- --- --- --- --- --- --- --- --- --- --- --- --- --- --- --- --- ---
    S   L   T   C   A   V   Y   G   G   S   L   S   G   Y   F   W   T   W 117                126                135                144                153                162
   ATC CGC CAG TCC CCC GGG AAG GGG CTG GAG TGG ATT GGG GAA AGC AAT TAT AGT
   --- --- --- --- --- --- --- --- --- --- --- --- --- --- --- --- --- ---
    I   R   Q   S   P   G   K   G   L   E   W   I   G   E   S   N   Y   S 171                180                189                198                207                216
   GGA AGT ACC AGG TAC AAC CCG TCC CTC AAG AGT CGA GTC ACC ATA TCA GTA GAC
   --- --- --- --- --- --- --- --- --- --- --- --- --- --- --- --- --- ---
    G   S   T   R   Y   N   P   S   L   K   S   R   V   T   I   S   V   D 225                234                243                252                261                270
   ACG TCC CAG AAC CAG TTC TCC CTG AAG CTG AGC TCT GTG ACC GCC GCG GAC ACG
   --- --- --- --- --- --- --- --- --- --- --- --- --- --- --- --- --- ---
    T   S   Q   N   Q   F   S   L   K   L   S   S   V   T   A   A   D   T 279                288                297                306                315                324
   GCT GTA TAT TAC TGT GCG AGA GGT TGG GCG GTG GAC GGT ATG GAC GTC TGG GGC
   --- --- --- --- --- --- --- --- --- --- --- --- --- --- --- --- --- ---
    A   V   Y   Y   C   A   R   G   W   A   V   D   G   M   D   V   W   G 333                342                351
   CAA GGG ACC ACG GTC ACC GTC TCC TCA 3'
   --- --- --- --- --- --- --- --- ---
    Q   G   T   T   V   T   V   S   S
```

Figure 6

SEQUENCE LISTING

```
<160> NUMBER OF SEQ ID NOS: 22

<210> SEQ ID NO 1
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 1 tct tac gag ctc acg cag ccg ccc tcg gtg tca gtg tcc cca gga cag        48
Ser Tyr Glu Leu Thr Gln Pro Pro Ser Val Ser Val Ser Pro Gly Gln
1               5                   10                  15 acg gcc agg atc acc tgc tct gga gat gca ttg cca aag caa tat gct        96
Thr Ala Arg Ile Thr Cys Ser Gly Asp Ala Leu Pro Lys Gln Tyr Ala
                20                  25                  30 tac tgg tat cag cag aag cca ggc cag gcc cct gtg ttg gtg ata tat       144
Tyr Trp Tyr Gln Gln Lys Pro Gly Gln Ala Pro Val Leu Val Ile Tyr
            35                  40                  45 aaa gat aat gag agg ccc tca ggg atc cct gag cga ttc tct ggc tcc       192
Lys Asp Asn Glu Arg Pro Ser Gly Ile Pro Glu Arg Phe Ser Gly Ser
        50                  55                  60 agg tca ggg aca aca gtc acg ttg acc atc agt gga gtc cag gca gaa       240
Arg Ser Gly Thr Thr Val Thr Leu Thr Ile Ser Gly Val Gln Ala Glu
65                  70                  75                  80 gac gag gct gac tat tac tgt caa tca gca gac agc agt ggt tct tcc       288
Asp Glu Ala Asp Tyr Tyr Cys Gln Ser Ala Asp Ser Ser Gly Ser Ser
                85                  90                  95 tgg gtg ttc ggc gga ggg acc aag ctg acc gtc cta                       324
Trp Val Phe Gly Gly Gly Thr Lys Leu Thr Val Leu
                100                 105

<210> SEQ ID NO 2
<211> LENGTH: 108
<212> TYPE: PRT
<213> ORGANISM: Homo sapiens

<400> SEQUENCE: 2
```

```
Ser Tyr Glu Leu Thr Gln Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Gln Arg Phe Ser Gly Ser
50                  55                  60

Arg Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ser Ser
                85                  90                  95

Trp Val Phe Gly Gly Gly Thr Lys Leu Thr Val Leu
            100                 105
```

```
<210> SEQ ID NO 3
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 3 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc tta agt ggt tac      96
Thr Leu Ser Leu Thr Cys Ala Val Tyr Gly Gly Ser Leu Ser Gly Tyr
            20                  25                  30 ttc tgg acc tgg atc cgc cag tcc ccc ggg aag ggg ctg gag tgg att     144
Phe Trp Thr Trp Ile Arg Gln Ser Pro Gly Lys Gly Leu Glu Trp Ile
        35                  40                  45 ggg gaa agc aat tat agt gga agt acc agg tac aac ccg tcc ctc aag     192
Gly Glu Ser Asn Tyr Ser Gly Ser Thr Arg Tyr Asn Pro Ser Leu Lys
50                  55                  60 agt cga gtc acc ata tca gta gac acg tcc cag aac cag ttc tcc ctg     240
Ser Arg Val Thr Ile Ser Val Asp Thr Ser Gln Asn Gln Phe Ser Leu
65                  70                  75                  80 aag ctg agc tct gtg acc gcc gcg gac acg gct gta tat tac tgt gcg     288
Lys Leu Ser Ser Val Thr Ala Ala Asp Thr Ala Val Tyr Tyr Cys Ala
                85                  90                  95 aga ggt tgg gcg gtg gac ggt atg gac gtc tgg ggc caa ggg acc acg     336
Arg Gly Trp Ala Val Asp Gly Met Asp Val Trp Gly Gln Gly Thr Thr
            100                 105                 110 gtc acc gtc tcc tca                                                  351
Val Thr Val Ser Ser
            115
```

```
<210> SEQ ID NO 4
<211> LENGTH: 117
<212> TYPE: PRT
<213> ORGANISM: Homo sapiens

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30
```

-continued

```
Phe Trp Thr Trp Ile Arg Gln Ser Pro Gly Lys Gly Leu Glu Trp Ile
        35                  40                  45
Gly Glu Ser Asn Tyr Ser Gly Ser Thr Arg Tyr Asn Pro Ser Leu Lys
    50                  55                  60
Ser Arg Val Thr Ile Ser Val Asp Thr Ser Gln Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Trp Ala Val Asp Gly Met Asp Val Trp Gly Gln Gly Thr Thr
            100                 105                 110
Val Thr Val Ser Ser
        115

<210> SEQ ID NO 5
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 5 tcc tct gag ctg aca cag cca ccc tcg gtg tca gtg tcc cca gga cag    48
Ser Ser Glu Leu Thr Gln Pro Pro Ser Val Ser Val Ser Pro Gly Gln
1               5                   10                  15 acg gcc agg atc acc tgc tct gga gat gca ttg cca aag caa tat gct    96
Thr Ala Arg Ile Thr Cys Ser Gly Asp Ala Leu Pro Lys Gln Tyr Ala
            20                  25                  30 tac tgg tat cag cag aag cca ggc cag gcc cct gtg ttg gtg ata tat   144
Tyr Trp Tyr Gln Gln Lys Pro Gly Gln Ala Pro Val Leu Val Ile Tyr
        35                  40                  45 aaa gat aat gag agg ccc tca ggg atc cct gag cga ttc tct ggc tcc   192
Lys Asp Asn Glu Arg Pro Ser Gly Ile Pro Glu Arg Phe Ser Gly Ser
    50                  55                  60 agg tca ggg aca aca gtc acg ttg acc atc agt gga gtc cag gca gaa   240
Arg Ser Gly Thr Thr Val Thr Leu Thr Ile Ser Gly Val Gln Ala Glu
65                  70                  75                  80 gac gag gct gac tat tac tgt caa tca gca gac agc agt ggt tct tcc   288
Asp Glu Ala Asp Tyr Tyr Cys Gln Ser Ala Asp Ser Ser Gly Ser Ser
                85                  90                  95 tgg gtg ttc ggc gga ggg acc aag ctg acc gtc cta                   324
Trp Val Phe Gly Gly Gly Thr Lys Leu Thr Val Leu
            100                 105

<210> SEQ ID NO 6
<211> LENGTH: 108
<212> TYPE: PRT
<213> ORGANISM: Homo sapiens

<400> SEQUENCE: 6

Ser Ser Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Glu Arg Phe Ser Gly Ser
    50                  55                  60

Arg Ser Gly Thr Thr Val Thr Leu Thr Ile Ser Gly Val Gln Ala Glu
65                  70                  75                  80
```

```
Asp Glu Ala Asp Tyr Tyr Cys Gln Ser Ala Asp Ser Ser Gly Ser Ser
            85                  90                  95

Trp Val Phe Gly Gly Gly Thr Lys Leu Thr Val Leu
            100                 105

<210> SEQ ID NO 7
<211> LENGTH: 34
<212> TYPE: DNA
<213> ORGANISM: Artificial Sequence
<220> FEATURE:
<223> OTHER INFORMATION: Poly C Sense Primer-5' AncTail

<400> SEQUENCE: 7
cgtcgatgag ctctagaatt cccccccccc cccc                              34

<210> SEQ ID NO 8
<211> LENGTH: 22
<212> TYPE: DNA
<213> ORGANISM: Artificial Sequence
<220> FEATURE:
<223> OTHER INFORMATION: 5'-VH Primer Set: VH1, 3, 5, 7

<400> SEQUENCE: 8
aggtgcagct gctcgagtct gg                                           22

<210> SEQ ID NO 9
<211> LENGTH: 23
<212> TYPE: DNA
<213> ORGANISM: Artificial Sequence
<220> FEATURE:
<223> OTHER INFORMATION: 5'-VH Primer Set: VH2
<220> FEATURE:
<221> NAME/KEY: misc_feature
<222> LOCATION: (4)..(4)
<223> OTHER INFORMATION: "n" is "a" or "g"

<400> SEQUENCE: 9
cagntcacct tgctcgagtc tgg                                          23

<210> SEQ ID NO 10
<211> LENGTH: 23
<212> TYPE: DNA
<213> ORGANISM: Artificial Sequence
<220> FEATURE:
<223> OTHER INFORMATION: 5'-VH Primer Set: VH4

<400> SEQUENCE: 10
caggtgcagc tgctcgagtc ggg                                          23

<210> SEQ ID NO 11
<211> LENGTH: 23
<212> TYPE: DNA
<213> ORGANISM: Artificial Sequence
<220> FEATURE:
<223> OTHER INFORMATION: 5'-VH Primer Set: VH4B

<400> SEQUENCE: 11
caggtgcagc tactcgagtg ggg                                          23

<210> SEQ ID NO 12
<211> LENGTH: 23
<212> TYPE: DNA
<213> ORGANISM: Artificial Sequence
<220> FEATURE:
<223> OTHER INFORMATION: 5'-VH Primer Set: VH6
```

<400> SEQUENCE: 12
caggtacagc tgctcgagtc agg                                            23

<210> SEQ ID NO 13
<211> LENGTH: 29
<212> TYPE: DNA
<213> ORGANISM: Artificial Sequence
<220> FEATURE:
<223> OTHER INFORMATION: 3'-VH Primer: CGd1

<400> SEQUENCE: 13
gcatgtacta gttttgtcac aagatttgg                                      29

<210> SEQ ID NO 14
<211> LENGTH: 24
<212> TYPE: DNA
<213> ORGANISM: Artificial Sequence
<220> FEATURE:
<223> OTHER INFORMATION: 5'-VL Primer Set: VL1

<400> SEQUENCE: 14
aattttgagc tcactcagcc ccac                                           24

<210> SEQ ID NO 15
<211> LENGTH: 27
<212> TYPE: DNA
<213> ORGANISM: Artificial Sequence
<220> FEATURE:
<223> OTHER INFORMATION: 5'-VL Primer Set: VL2

<400> SEQUENCE: 15
tctgccgagc tccagcctgc ctccgtg                                        27

<210> SEQ ID NO 16
<211> LENGTH: 27
<212> TYPE: DNA
<213> ORGANISM: Artificial Sequence
<220> FEATURE:
<223> OTHER INFORMATION: 5'-VL Primer Set: VL3

<400> SEQUENCE: 16
tctgtggagc tccagccgcc ctcagtg                                        27

<210> SEQ ID NO 17
<211> LENGTH: 33
<212> TYPE: DNA
<213> ORGANISM: Artificial Sequence
<220> FEATURE:
<223> OTHER INFORMATION: 5'-VL Primer Set: VL4

<400> SEQUENCE: 17
tctgaagagc tccaggaccc tgttgtgtct gtg                                 33

<210> SEQ ID NO 18
<211> LENGTH: 24
<212> TYPE: DNA
<213> ORGANISM: Artificial Sequence
<220> FEATURE:
<223> OTHER INFORMATION: 5'-VL Primer Set: VL5

<400> SEQUENCE: 18
cagtctgagc tcacgcagcc gccc                                           24

<210> SEQ ID NO 19
<211> LENGTH: 24

```
<212> TYPE: DNA
<213> ORGANISM: Artificial Sequence
<220> FEATURE:
<223> OTHER INFORMATION: 5'-VL Primer Set: VL6

<400> SEQUENCE: 19
cagactgagc tcactcagga gccc                                              24

<210> SEQ ID NO 20
<211> LENGTH: 24
<212> TYPE: DNA
<213> ORGANISM: Artificial Sequence
<220> FEATURE:
<223> OTHER INFORMATION: 5'-VL Primer Set: VL7

<400> SEQUENCE: 20
caggttgagc tcactcaacc gccc                                              24

<210> SEQ ID NO 21
<211> LENGTH: 27
<212> TYPE: DNA
<213> ORGANISM: Artificial Sequence
<220> FEATURE:
<223> OTHER INFORMATION: 5'-VL Primer Set: VL8

<400> SEQUENCE: 21
caggctgagc tcactcagcc gtcttcc                                           27

<210> SEQ ID NO 22
<211> LENGTH: 30
<212> TYPE: DNA
<213> ORGANISM: Artificial Sequence
<220> FEATURE:
<223> OTHER INFORMATION: 3'-VL Primer: CL2

<400> SEQUENCE: 22
cgccgtctag aattatgaac attctgtagg                                        30
```

ANTI HEPATITIS C VIRUS ANTIBODY AND USES THEREOF

The present application is a divisional patent application of U.S. Ser. No. 09/744,176, now U.S. Pat. No. 6,951,646, filed Jun. 18, 2001.

FIELD OF THE INVENTION

The present invention concerns human antibodies capable of specifically binding to conformation-dependent epitopes of Hepatitis C virus (HCV) glycoprotein E2 and various uses thereof.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

Hepatitis C virus (HCV) is the principal causative agent for non-A, non-B Hepatitis. The prevalence of HCV infection in the blood donor population has been estimated to range from 0.4 to 2% (Choo et al., 1989). Acute HCV infection leads, in more than 70% of the patients, to the development of chronic hepatitis that can evolve towards cirrhosis and hepatocellular carcinoma (Saito et al., 1990). HCV is an enveloped positive-stranded RNA virus which is classified in the Flaviviridae family (Francki et al., 1991, Miller et al., 1990). It contains a genome of about 9,500 nts encoding a polyprotein of 3010 to 3033 amino acids. Processing of the polyprotein by host and viral proteases results in the production of structural and nonstructural (NS) proteins (Rice et al., 1996). Structural proteins include a nucleocapsid and two putative virion envelope glycoproteins E1 and E2 (Miyamura et al., 1993). Non-structural proteins include NS2 to NS5 antigens.

In some individuals, acute infection successfully resolves indicating that HCV can be controlled by the host immune system. The mechanisms by which the host overcomes HCV infection remain unknown. Previous reports strongly suggest that humans and chimpanzees can generate virus-neutralizing antibodies (Choo et al., 1994, Farci et al., 1994, 1996, Shimizu et al., 1994). Successful in vivo protection of chimpanzees from primary infection by an homologous HCV isolate has been achieved following immunization with recombinant E1 and E2 proteins (Choo et al., 1994). In that study only those chimpanzees showing high anti-E2 antibody titers were protected. While neutralizing antigenic domains were not identified, it was postulated that conformation of the immunogens was critical for the induction of neutralizing antibodies.

As there is to date no efficient in vitro replication system to grow the virus and develop neutralization assays, alternative assays to assess the biological function of anti-E1/E2 antibodies are actively searched for. Prevention of viral attachment onto presumed susceptible cells has been described in preliminary studies (Shimizu et al., 1994, Zibert et al., 1995). More recently, an "in vitro" neutralization of binding (NOB) assay has been developed that is exploiting the specific binding of a highly purified E2 protein onto susceptible target cells (Rosa et al., 1996). This assay allows the quantitative evaluation of NOB antibodies that are capable of neutralizing the binding of E2 onto such cells. Using this system, Rosa et al., have shown that only those chimpanzees immunized with E1 and E2 proteins that developed high anti-NOB titers were protected against challenged infection (Rosa et al., 1996), suggesting that NOB activity could be an indication for "in vivo" neutralization of viral infection. In HIV infection, a similar model has recently shown that affinity of antibody binding to envelope glycoprotein oligomers was a good predictor for virus neutralization (Fouts et al., 1997). Another way to assess the biological activity of anti-E1 and/ or anti-E2 antibodies consists in testing the ability of such antibodies to recognize native structures believed to exist on the surface of virions. In vitro studies have shown that E1 and E2 interact to form non-covalently linked complexes (Deleersnyder et al., 1997, Ralston et al., 1993). Such complexes have been proposed to represent functional subunits of HCV virions (Deleersnyder et al., 1997, Dubuisson et al., 1994, Dubuisson and Rice, 1996, Ralston et al., 1993). Probing for the B-cell repertoire in viral infections is critical for the understanding of pathogenesis associated with these infections. Human monoclonal antibodies provide an alternative method to do so. Isolation and characterization of such antibodies have been reported in the case of HCV for only a limited number of viral antigens. These include the nucleocapsid, the NS3 and NS4 proteins (Akatsuka et al., 1993, Cerino et al., 1991, 1993, Chan et al., 1996, Mondelli et al., 1994) and more recently the glycoprotein E2 (Chan et al., 1996). In this latter case, authors used the phage display technology coupled with the use of synthetic peptides for the screening of the anti-E2 immune reactivity and were able to obtain specific IgG single-chain Fvs that recognized the E2 sequence. While a specific linear epitope sequence was identified, no biological activity for the anti-E2 antibody was described and the putative role of this antibody in the control or progression of infection remains undefined. Recently, WO97/40176 described immunoglobulin molecules obtained from a combinatorial library, which are capable of specifically binding with HCV E2 antigen. Although Fab-fragments of such immunoglobulins were demonstrated to have binding activity in a neutralization of binding assay recombinantly expressed Fab clones and corresponding whole IgG molecules were found to be negative in neutralizing the binding of the HCV E2 polypeptide.

SUMMARY OF THE INVENTION

The present invention relates to novel antibodies comprising at least one complementarity determining region (CDR) of the variable domain of a human antibody which is capable of specifically recognizing a conformation dependent epitope of HCV glycoprotein E2. Furthermore, the present invention relates to antigens recognized by said antibodies. In addition, the present invention relates to a polynucleotide encoding the above-described antibody or antigen, vectors comprising said polynucleotide as well as cells comprising the afore-mentioned polynucleotide or vector. A further aspect of the invention is a method for preparing antibodies capable of recognizing conformation dependent epitopes of HCV glycoprotein E2 and that are capable of neutralizing the binding of the E2 protein onto susceptible cells. The present invention further involves pharmaceutical and diagnostic compositions comprising the afore-mentioned antibodies, antigens, polynucleotides, vectors or cells as well as the use of the afore-described compounds in various therapeutic and diagnostic applications.

DETAILED DESCRIPTION OF THE PRESENT INVENTION

Accordingly, the technical problem of the invention is to provide means and methods for the treatment and prevention of HCV infection in humans.

The solution to this technical problem is achieved by providing the embodiments characterized in the claims, namely antibodies are provided that 1) recognize conformation-dependent determinant(s), 2) were capable of recognizing antigens derived from different HCV genotypes and 3) were able to precipitate noncovalently associated E1 E2 complexes believed to exist on the surface of virion particles; and 4) are capable of neutralizing the binding of E2 protein onto susceptible cells suggesting the potential of the antibodies for in vivo neutralization. Such antibodies are particularly useful for the development of therapeutic or preventive strategies to fight infection by a highly mutable agent such as HCV.

Accordingly, the invention relates to an antibody comprising at least one (preferably two, more preferably three, four or five, and most preferably six) complementarity determining region (CDR) of the $V_H$ and/or $V_L$ region of a human antibody comprising the amino acid sequence encoded by the DNA sequence depicted in FIG. 5 ($V_L$) (SEQ ID NO: 1) and FIG. 6 ($V_H$) (SEQ ID NO: 3) that specifically recognizes a conformation-dependent epitope of Hepatitis C Virus glycoprotein E2 and is capable of precipitating covalently or non-covalently associated E2/E1 complexes. Alternatively, and/or in addition the antibody of the invention comprises at least 1, 2 or 3 CDR(s) of the $V_L$ region of a human immunoglobulin chain comprising the amino acid sequence of SEQ ID NO: 6 and encoded by the DNA sequence depicted in SEQ ID NO: 5 which represents an allelic variant of the $V_L$ encoding DNA sequence of SEQ ID NO: 1 (FIG. 5).

The person skilled in the art knew that each variable domain (the heavy chain $V_H$ and light chain $V_L$) of an antibody comprises three hypervariable regions, sometimes called complementarity determining regions or "CDRs" flanked by four relatively conserved framework regions or "FRs". The CDRs contained in the variable regions of the antibody of the invention can be determined, e.g., according to Kabat, Sequences of Proteins of Immunological Interest (U.S. Department of Health and Human Services, third edition, 1983, fourth edition, 1987, fifth edition 1990). The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously has substantially the same or similar binding properties as the antibody described in the appended examples. The person skilled in the art will readily appreciate that using the variable domains or CDRs described above antibodies can be constructed according to methods known in the art, e.g., as described in EP-A1 0 451 216 and EP-A1 0 549 581.

The term "conformation-dependent epitope of Hepatitis C Virus glycoprotein E2" denotes the non-linear nature of the epitope recognized by the antibody of the invention. This means that the antigen's determinants of the epitope are provided by the three-dimensional structure of the HCV glycoprotein E2 rather than by the amino acid sequence as such.

The term "capable of precipitating covalently or non-covalently associated E2/E1 complexes" refers to the ability of the antibody of the invention to precipitate E1 and E2 noncovalently associated complexes which are believed to exist on the virion particle.

The term "capable of neutralizing the binding of E2 protein onto susceptible cells" describes the ability of candidate antibodies to neutralize the binding of highly purified E2 (neutralizing of binding or NOB) onto cells susceptible to HCV infection; see also Example 4. Advantageously, the antibody of the invention has an NOB activity at a concentration of about 1 µg/ml, preferably at a concentration of about 0.1 µg/ml and most preferably at a concentration of about 0.03 µg/ml.

In accordance with the present invention a screening assay that specifically allows the detection of anti-E2 antibodies capable of recognizing E2 directly expressed in cells without the requirement of antigen purification was chosen to identify and purify antibodies directed at conformation-dependent determinants. The assay was also based on expression of a genotype 1a derived antigen thus allowing for the characterization of cross-reactive anti-E2 antibodies and epitopes. Using this approach, two clones have been obtained producing anti-E2 antibodies from two HCV chronically infected patients. The first clone (clone 503) was obtained from one patient (patient 1) infected by a genotype 4 isolate while the second clone (clone 108) was derived from a second patient (patient 2) infected by a genotype 1 b isolate. It could be shown that the HMabs displayed in addition a good reactivity against a genotype 1 b antigen suggesting that the determinant(s) targeted by these antibodies are conserved among at least two of the main prevalent viral subtypes found in the world (subtypes 1a and 1b). In view of the above, it can be reasonably expected that the antibody of the present invention is also capable of reacting with antigens of other genotypes such as 2, 3a, 4, 5 and/or 6. The binding activity of an antibody of the invention concerning these genotypes can be easily tested in accordance with the methods as described in the examples.

The results obtained in accordance with the present invention indicate that the determinants recognized by the HMabs of the invention are targeted at conformation-dependent domains of E2 since linear determinants using different screening approaches, including peptide-scanning, Western-blots and immunofluorescence analysis using expressed truncated domains of the protein could not be identified; see Example 2. On the other hand, immunoprecipitation studies performed under reducing or non-reducing conditions indicated that the HMabs recognized a conformation-dependent-determinant. Under non-reducing conditions, these antibodies precipitated covalently as well as noncovalently associated E1 E2 complexes; see Example 3.2. The latter are thought to be functional subunits incorporated in the virion particle (Deleersnyder et al., 1997). The present data, in particular obtained from kinetic analysis of epitope formation strongly indicate that the two HMabs recognize domains of the E2 protein that appear to be folded early. Such domains would stay accessible as the protein further matures, until it adopts its final conformation characteristic of the form of E2 susceptible to be present on the surface of virions. The kinetic analysis, together with the NOB data (i.e. antibody 503, displaying NOB activity) also suggest that the two antibodies recognize different determinants; see Example 4. Alternatively, that affinity of the antibodies for the E2 protein differs.

The most encouraging result obtained in accordance with the present invention was the demonstration that one of the HMabs displayed strong NOB activity. These observations together with Rosa's et al. (Rosa et al., 1996), indicate that the determinant(s) recognized by NOB antibodies are likely directed at conformation-dependent domains of E2, domains that appear to be conserved between different genotypes. Such domains seem to be distinct from the hypervariable region 1 (HVR) that has been shown to contain neutralization epitopes. In a recent study, Zibert et al. (Zibert et al., 1997) have been able to correlate early appearance of antibodies directed at a non-conformational structure found in the HVR with acute self-limited infection. Results from the study suggests the critical existence and role of antibodies directed at a linear determinant of E2 in the control of HCV infection, observations that are in agreement with a study originally performed in the chimpanzee model by Farci et al. (Farci et al., 1996). Authors in this latter study generated a hyperimmune serum directed at a peptide from the HVR, serum that contained antibodies capable to neutralize the infectivity of a well characterized inoculum in vitro. A similar experiment was also performed by Shimizu et al. (Shimizu et al., 1996). Thus, all of these studies strongly suggest that neutralization of HCV would mostly be type-specific involving the participation of variable, non-conserved epitopes. Nonetheless, recent observations have begun to suggest the existence of other neutralization determinants, cross reactive and not directed at the HVR. In the vaccination study by Choo et al., induced neutralizing antibodies were not directed at the HVR of E2 but apparently at other determinants carried by the antigen (Choo et al., 1994). Abrignani has recently observed a correlation between spontaneous resolution of chronic infection and appearance of high anti-NOB antibody titers (Abrignani 1997). In patients described in the Examples hereinafter, high or measurable neutralization of binding of E2 was not restricted to sera from patients infected with genotype 1a isolates, thus suggesting the existence of cross-reactive epitopes such as those described in the present application. As it was difficult to find a direct correlation between NOB titers of a purified MAb and titers found in patients sera (both patients in our study had similar NOB serum titers>1:1000), it was surprising that antibody 503 has an NOB activity detectable at very low concentration (0.03 μg/ml) providing for a potent activity; see Example 4.

The HMAbs produced in accordance with the present invention are expected to be useful tools to study further the biogenesis, folding and assembly of HCV glycoproteins as well as for characterization of the virion structure and a putative cell-surface receptor. As the antibody of the invention exemplified by Ab 503 represents the first HMAb described to date as having NOB activity, this antibody is particularly useful for passive immunization studies. Antibody infusion studies have demonstrated, in the case of lentiviruses, a beneficial role of administered neutralizing antibodies in the control and even the prevention of infection in different animal models (Conley et al., 1996, Emini et al., 1992, Putkonen et al., 1991).

In a preferred embodiment of the invention, said antibody is a monoclonal antibody, a polyclonal antibody, a single chain antibody, humanized antibody, or fragment thereof that specifically binds said HCV E2 glycoprotein also including bispecific antibody, synthetic antibody, antibody fragment, such as Fab, Fv or scFv fragments etc., or a chemically modified derivative of any of these. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned epitopes can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the conformation-dependent HCV glycoprotein E2 epitope (Schier, Human Antibodies Hybridomas 7 (1996), 97-105; Malmborg, J. Immunol. Methods 183 (1995), 7-13). The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)2, as well as in single chains; see e.g. WO88/09344. In case of bispecific antibodies where one specificity is directed to an HCV E2 glycoprotein epitope and the other preferably to a T cell antigen such as CD3, it is advantageous if the binding site recognizing the viral epitope has a high affinity in order to capture the virus or target cells which have been infected with HCV and can be destroyed with high efficiency. On the other hand, the binding affinity of the binding site recognizing, e.g., a T cell should be in the order of those of the natural T cell receptor/ligand interaction or of that usually found for the interaction of the T-cell costimulatory molecules with their receptor.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

In a particularly preferred embodiment, the antibody of the invention comprises the amino acid sequence of the $V_H$ and/or $V_L$ region as depicted in FIGS. 5 and 6, respectively.

In a further embodiment, the present invention relates to an antigen or an epitope thereof which is recognized by an antibody of the invention. Said antigen or epitope may be glycosylated, unglycosylated or partially deglycosylated. As discussed herein and explained in the examples, the present invention feature novel antigens, recognized by the aforedescribed antibodies. For the identification and isolation of antigen and epitopes of the invention, e.g., cDNA libraries can be screened by injecting various cDNAs into oocytes, allowing sufficient time for expression of the cDNA gene products to occur, and testing for the presence of the desired cDNA expression product, for example, by using the antibody of the invention.

Alternatively, a cDNA expression library in *E. coli* can be screened indirectly for peptides having at least one epitope of the invention using antibodies of the invention (Chang and Gottlieb, J. Neurosci., 8:2123, 1988). After having revealed the structure of such antigens the rational design of binding partners and/or domains may be possible. For example, folding simulations and computer redesign of structural motifs can be performed using appropriate computer programs (Olszewski, Proteins 25 (1996), 286-299; Hoffman, Comput. Appl. Biosci. 11 (1995), 675-679). Furthermore, computers can be used for the conformational and energetic analysis of detailed protein models (Monge, J. Mol. Biol. 247 (1995), 995-1012; Renouf, Adv. Exp. Med. Biol. 376 (1995), 37-45).

In another embodiment the present invention relates to a polynucleotide encoding at least a variable region of an immunoglobulin chain of any of the before described antibodies of the invention. One form of immunoglobulin constitutes the basic structural unit of an antibody. This form is a tetramer and consists of two identical pairs of immunoglobulin chains, each pair having one light and one heavy chain. In each pair, the light and heavy chain variable regions or domains are together responsible for binding to an antigen, and the constant regions are responsible for the antibody effector functions. In addition to antibodies, immunoglobulins may exist in a variety of other forms (including less than full-length that retain the desired activities), including, for example, Fv, Fab, and F(ab')2, as well as single chain antibodies (e.g., Huston, Proc. Nat. Acad. Sci. USA 85 (1988), 5879-5883 and Bird, Science 242(1988), 423-426); see also supra. An immunoglobulin light or heavy chain variable domain consists of a "framework" region interrupted by three hypervariable regions, also called CDR's; see supra.

The antibodies of the present invention can be produced by expressing recombinant DNA segments encoding the heavy and light immunoglobulin chain(s) of the antibody invention either alone or in combination.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. Preferably said polynucleotide is part of a vector. Such vectors may comprise further genes such as marker genes which allow for the selection of said vector in a suitable host cell and under suitable conditions. Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the PL, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979); see also, e.g., the appended examples.

As described above, the polynucleotide of the invention can be used alone or as part of a vector to express the (poly) peptide of the invention in cells, for, e.g., gene therapy or diagnostics of diseases related to HCV infection. The polynucleotides or vectors of the invention are introduced into the cells which in turn produce the antibody. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Furthermore, the present invention relates to vectors, particularly plasmids, cosmids, viruses and bacteriophages used conventionally in genetic engineering that comprise a polynucleotide encoding a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989).

Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally.

The host cell can be any prokaryotic or eukaryotic cell, such as a bacterial, insect, fungal, plant, animal or human cell. Preferred fungal cells are, for example, those of the genus Saccharomyces, in particular those of the species S. cerevisiae. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, E. coli, S. typhimurium, Serratia marcescens and Bacillus subtilis. The term "eukaryotic" is meant to include yeast, higher plant, insect and preferably mammalian cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic animals, preferably mammals, comprising cells of the invention may be used for the large scale production of the (poly)peptide of the invention.

Thus, in a further embodiment, the present invention relates to a method for the production of an antibody capable of recognizing a conformation-dependent epitope of Hepatitis C Virus glycoprotein E2 or a functional fragment or immunglobulin chain(s) thereof comprising
 (a) culturing the cell of the invention; and
 (b) isolating said antibody or functional fragment or immunoglobulin chain(s) thereof from the culture, The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporeally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen. Furthermore, the invention relates to an antibody of the invention or fragment thereof encoded by a polynucleotide according to the invention or obtainable by the above-described methods or from cells produced by the method described above. The antibodies of the present invention will typically find use individually in treating substantially any disease susceptible to monoclonal antibody-based therapy. In particular, the immunoglobulins can be used for passive immunization or the removal of HCV or unwanted cells or antigens, such as by complement mediated lysis, all without substantial immune reactions (e.g., anaphylactic shock) associated with many prior antibodies. For an antibody of the invention, typical disease states suitable for treatment include chronic HCV infection.

The antibodies, antigens and epitopes of the invention can be used therapeutically in, e.g., patients suffering from HCV infection. Such therapy can be accomplished by, for example, the administration of antibodies, antigens or epitopes of the invention. Such administration can utilize unlabeled as well as labeled antibodies or antigens. For example, when unlabeled the antigen or epitope is utilized advantageously, it would be in a form wherein, for example, the antigens are in fragments which are too small to stimulate an immune response, but large enough to bind, or block, the docking of HCV via E2 glycoprotein onto the target cells.

Alternatively, the antibodies, antigens and epitopes of the invention could be administered labeled with a therapeutic agent. These agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical crosslinking as described in, e.g., WO 94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The above described fusion protein may further comprise a cleavable linker or cleavage site for proteinases. These spacer moieties, in turn, can be either insoluble or soluble (Diener, et al., Science, 231:148, 1986) and can be selected to enable drug release from the antigen at the target site. Examples of therapeutic agents which can be coupled to the antibodies, antigens and epitopes of the invention for immunotherapy are drugs, radioisotopes, lectins, and toxins. The drugs with which can be conjugated to the antibodies, antigens and epitopes of the invention include compounds which are classically referred to as drugs such as mitomycin C, daunorubicin, and vinblastine. In using radioisotopically conjugated antibodies, antigens or epitopes of the invention for, e.g., immunotherapy, certain isotopes may be more preferable than others depending on such factors as leukocyte distribution as well as stability and emission. Depending on the autoimmune response, some emitters may be preferable to others. In general, α and β particle-emitting radioisotopes are preferred in immunotherapy. Preferred are short range, high energy α emitters such as $^{212}$Bi. Examples of radioisotopes which can be bound to the antibodies, antigens or epitopes of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody, antigen or epitope of the invention, as well as ex vivo and in vivo therapeutic protocols, are known, or can be easily ascertained, by those of ordinary skill in the art. Wherever appropriate the person skilled in the art may use a polynucleotide of the invention encoding any one of the above described antibodies, antigens or epitopes or the corresponding vectors instead of the proteinaeous material itself.

Moreover, the present invention relates to pharmaceutical compositions comprising the aforementioned antibody, antigen or epitope, polynucleotide, vector or cell of the invention. The pharmaceutical composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition. For example, the pharmaceutical compositions of the invention, as described above, may be administered in combination with other anti viral agents. Such agents may include, as a non limiting example, interferons, other anti HCV monoclonal or polyclonal antibodies, nucleoside analogs, inhibitors of DNA polymerase, and agents as described in Example 6. In the case of such a combination therapy the antibodies may be given simultaneously with the anti viral agent or sequentially either before or after treatment with the anti viral agent. Such pharmaceutical compositions may also be used, for example, for immunization of liver transplantation patients to eliminate possible recurrent HCV infections in such patients. Furthermore, the pharmaceutical composition may be formulated as a vaccine, for example, if the pharmaceutical composition of the invention comprises an antigen as described above that is capable of eliciting an effective immune response against HCV. Advantageously, the pharmaceutical composition of the invention is intended for use in liver transplantation. Furthermore, it is expected that the antibody of the invention is useful for the prevention of infection of Tupaia-hepatocytes with HCV-infectious human sera.

It is envisaged by the present invention that the various polynucleotides and vectors of the invention are administered either alone or in any combination using standard vectors and/or gene delivery systems, and optionally together with a pharmaceutically acceptable carrier or excipient. Subsequent to administration, said polynucleotides or vectors may be stably integrated into the genome of the subject. On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying of HCV infection. Furthermore, it is possible to use a pharmaceutical composition of the invention which comprises polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others; see also supra. Delivery of nucleic acids to a specific site in the body for gene therapy may also be accomplished using a biolistic delivery system, such as that described by Williams (Proc. Natl. Acad. Sci. USA 88 (1991), 2726-2729).

In a further embodiment the present invention relates to a method for preventing (re)infection of Hepatitis C Virus in a subject, comprising the step of administering the antibody, polynucleotide or vector of the invention. Further encompassed is a method for alleviating chronic Hepatitis C in a subject, comprising the step of treating said subject using the afore-described compounds of the invention combined with a pharmaceutically acceptable carrier.

In another embodiment the present invention relates to a diagnostic composition comprising any one of the above described the antibodies, antigens, polynucleotides, vectors or cells of the invention and optionally suitable means for detection. The antigens and antibodies of the invention are, for example, suited for use in immunoassays in which they can be utilized in liquid phase or bound to a solid phase carrier. Examples of immunoassays which can utilize the antigen of the invention are competitive and non-competitive immunoassays in either a direct or indirect format. Examples of such immunoassays are the radioimmunoassay (RIA), the sandwich (immunometric assay) and the Western blot assay. The antigens and antibodies of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the antibodies of the invention may also be used in a method for the diagnosis of HCV infections in an individual by obtaining a body fluid sample from the tested individual which may be a blood sample, a lymph sample or any other body fluid sample and contacting the body fluid sample with an antibody of the invention under conditions enabling the formation of antibody-antigen complexes. The level of such complexes is then determined by methods known in the art, a level significantly higher than that formed in a control sample indicating an HCV infection in the tested individual. In the same manner, the specific antigen bound by the antibodies of the invention may also be used for diagnosis of HCV infection in an individual by contacting a body fluid sample from the tested individual with the antigen as described above and determining the formation of antigen-antibody complex in the sample. Thus, the present invention relates to an in vitro immunoassay for the presence of Hepatitis C Virus glycoprotein E2, characterized by measuring its co-precipitation with the antibody of the invention, preferably under non-reducing conditions. Furthermore, the present invention encompasses a method for diagnosing chronic Hepatitis C in a subject, characterized in that samples of said subject are tested using the antibody of the invention for the presence of neutralization of binding of Hepatitis C Virus glycoprotein E2 onto target cells. Accordingly, the present invention also involves a neutralization assay for inhibiting the binding of Hepatitits C Virus glycoprotein E2 onto target cells using the antibody of the invention.

The present invention also comprises methods of detecting the presence of HCV antigen in a sample, for example, a cell sample, which comprises obtaining a cell sample from a subject, contacting said sample with one of the aforementioned antibodies, preferably under non-reducing conditions permitting binding of the antibody to the antigen, and detecting the presence of the antibody so bound, for example, using immuno assay techniques such as radioimmunoassay or enzymeimmunoassay. Furthermore, the present invention relates to a method for detecting autoantibodies against Hepatitis C Virus in a subject comprising contacting a sample from a subject with the antigen of the invention, and detecting the presence of antibodies bound to said antigens.

In a still further preferred embodiment the present invention relates to the use of the afore-described antibody, antigen, polynucleotide, vector or cell for the preparation of a pharmaceutical composition for the treatment or prevention of HCV infection in a subject or for the prevention of recurrence of HCV infection. Preferably said pharmaceutical composition is designed to be administered prior, during or after liver transplantation.

The pharmaceutical compositions, methods and uses of the present invention may be desirably employed in humans, although animal treatment is also encompassed by the methods and uses described herein.

These and other embodiments are disclosed and encompassed by the description and Examples of the present invention. Further literature concerning any one of the antibodies, methods, uses and compounds to be employed in accordance with the present invention may be retrieved from pubic libraries and databases, using, for example, electronic devices. For example, the public database, "Medline," may be utilized which is available on the internet at the National Institutes of Health, National Library of Medicine website. Further databases and addresses, such as the National Institutes of Health and TIGR websites, are known to the person skilled in the art and can also be obtained using known and available search engines. An overview of patent information in biotechnology and a survey of relevant sources of patent information useful for retrospective searching and for current awareness is given in Berks, TIBTECH 12 (1994), 352-364.

The above disclosure generally describes the present invention. A more complete understanding can be obtained by reference to the following specific examples which are provided herein for purposes of illustration only and are not intended to limit the scope of the invention.

The Figures show:

FIG. 1: Indirect immunofluorescence analysis. CV-1 cells were infected with the SVE2 recombinant virus as previously described (Fournillier-Jacob et al., 1996) and immunofluorescence analysis performed using patients's sera (1:20 dilution) or supernatants from the HMAbs producing cell lines. Staining was performed using goat-anti human IgG immune serum coupled with fluoresceine. (A) serum from patient 1; (B) serum from patient 2; (C) HMAb 503; (D) HMAb 108; (E) serum from a patient with chronic hepatitis unrelated to HCV. An additional negative control (F) included CV-1 cells transfected with a SVE1 recombinant virus (expressing E1) and stained with the HMAb 503 or 108 (result is shown for HMAb 503 only).

Figure 2:
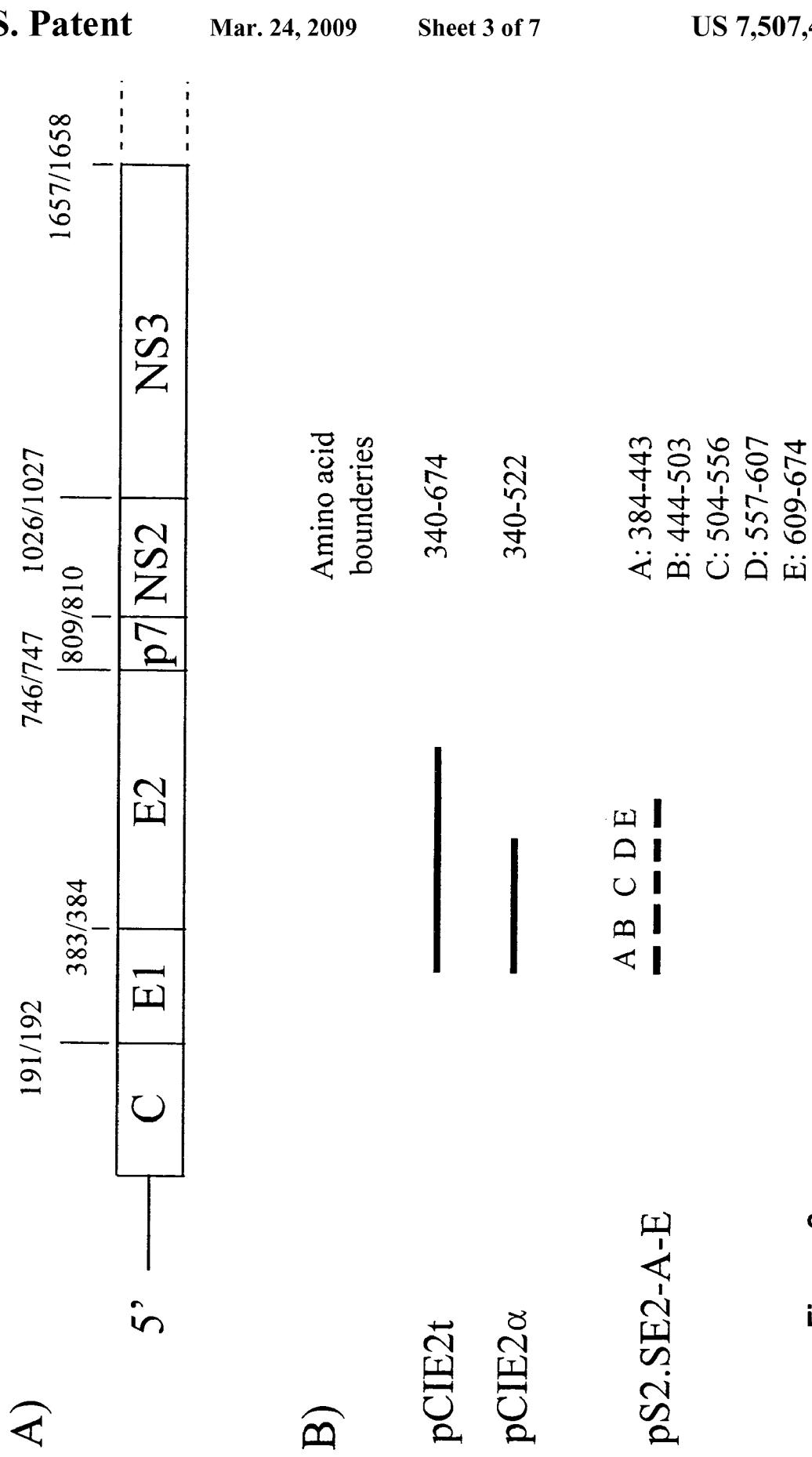

FIG. 2: Plasmids used in the epitope mapping studies. (A) Representation of the HCV genomic domain coding for the viral nucleocapsid (C), the glycoproteins E1 and E2 and the non-structural proteins p7, NS2 and NS3 (Rice et al., 1996). Amino acid position of the proteolytic cleavage sites are indicated. (B) Map position and amino acid boundaries of the sequences encoded by the different expression plasmids.

Figure 3:
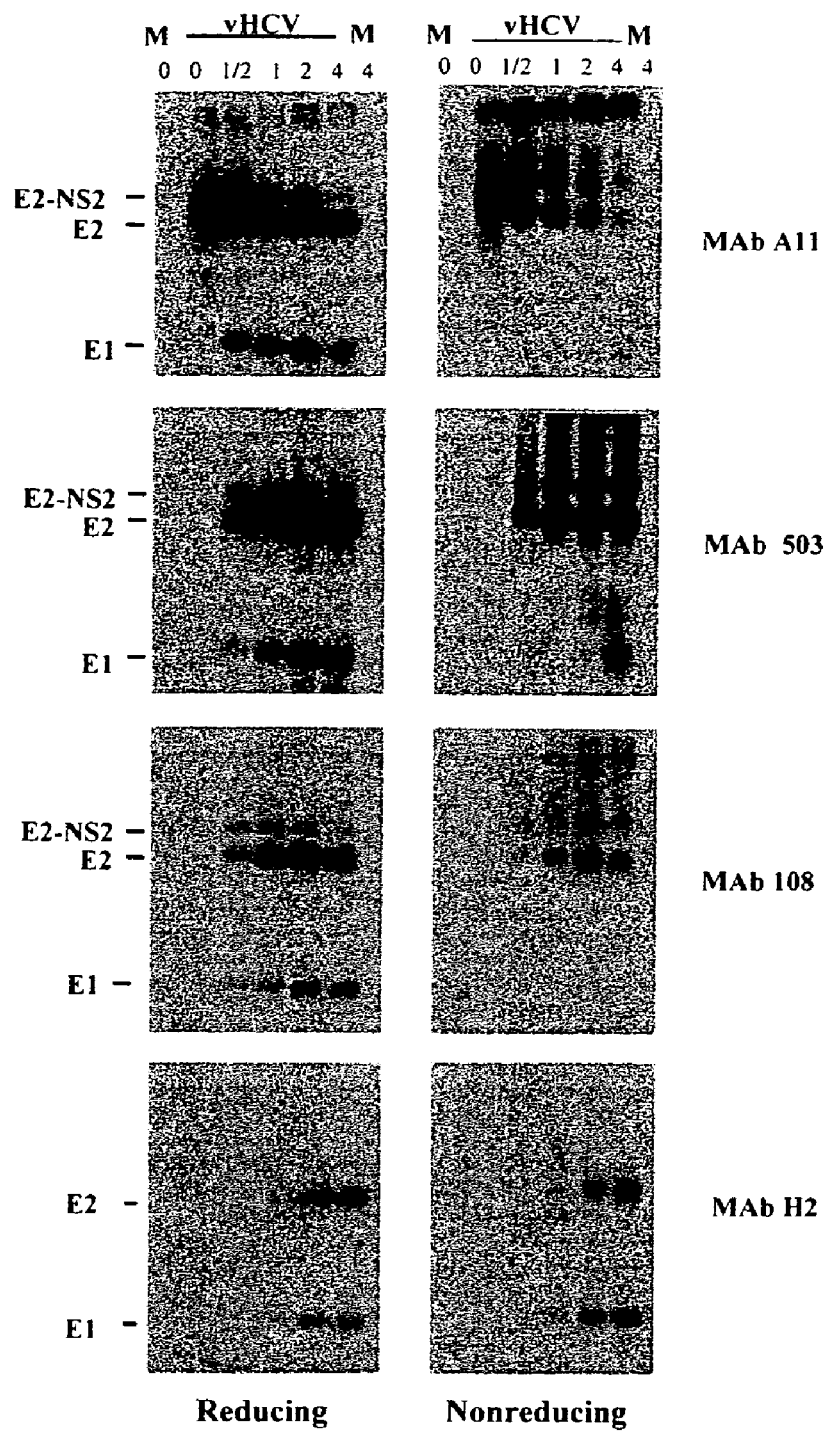

FIG. 3: Immunoprecipitation of E2 and co-precipitation of E1 and analysis of epitope formation under under reducing and non-reducing conditions. Cells coinfected with vTF7-3 and vHCV1-1488 (vHCV) or with TF7-3 alone (M) were pulse labeled for 5 min and chased for the indicated times (in hours). The E2 glycoprotein was immunoprecipitated with HMAbs 108, 503 and mouse MAbs H2 (Deleersnyder et al., 1997) and A11 (Dubuisson et al., 1994). Immunoprecipitates were analyzed under reducing or nonreducing conditions by SDS-PAGE (10% acrylamide).

Expected position of HCV specific proteins are indicated at the left of the figures.

FIG. 4: Percent neutralization of E2 binding by HCV-E2 HMAbs. Various concentrations of anti-E2 HMAbs 503 and 108 were tested for their ability to neutralize binding of purified CHO expressed E2 protein onto MOLT-4 cells. Neutralization was calculated as described (Rosa et al., 1996) and 50% neutralization titers are indicated.

FIG. 5: Nucleotide and amino acid sequences of the variable region of the light chain ($V_L$) of HMAb 503.

FIG. 6: Nucleotide and amino acid sequences of the variable region of the heavy chain ($V_H$) of HMAb 503.

The Examples illustrate the invention.

EXAMPLE 1

Patients' Screening and Generation of Human Monoclonal Antibody Producing B Cells (LCLs)

Two patients were enrolled in the study. HCV infection was determined by the RIBA III assay (Abbott Laboratories). At time of PBMC (peripheral blood mononuclear cells) immortalization, both patients had chronic hepatitis as determined by histological examination and positive PCR assays. Serum viral loads were determined using the bDNA assay version 2.0 (quantiplex HCV RNA Assay, Chiron Diagnostics). HCV genotypes were determined using three different methods. The first one was based on the detection of genotype-specific antibodies directed at the nonstructural antigen 4 (NS4) and was determined using the MUREX 1-6 serotyping assay according to the manufacturer's instruction (MUREX Diagnostics SA, Bhattacherjee et al., 1995). The second one was based on the amplification of viral sequences from the 5'noncoding region (NCR) of the genome using genotype/subtype specific primers and was performed using the INNO-LIPA assay (Innogenetics S.A.). In one of these two patients, patient 1, despite detectable HCV RNA by PCR in the serum, serum ALT (alanine amino transferase) levels were and remained normal (mild hepatitis). In contrast, ALT levels remained persistently elevated in patient 2 and infection in this patient was characterized by cirrhosis. Generation of HMAbs producing cell lines was performed as previously described (Boyer et al., 1991, Desgranges et al., 1988, Seigneurin et al., 1983). Briefly, after Ficoll isolation, PBMCs were exposed to EBV culture supernatant (1 ml of B95.8 strain supernatant with a titer of 10-3 TD50/ml for 5×106 PBMCs) at room temperature. After incubation, they were diluted in medium at concentration ranging from 50 to 100× 103 cells per well. After 2 to 4 weeks, the supernatants were screened for anti-E2 reactivity by the SVE2 CV-1 IFA. Detection of anti-E2 antibodies has been reported to be tightly dependent on the antigen production method (Chien et al., 1993, Hsu et al., 1993, Lesniewski et al., 1995). Eukaryotic but not prokaryotic expression of HCV E2 has been shown to allow for proper processing and glycosylation of the protein (Selby et al., 1993). In our study, we used as screening assay for anti-E2 antibodies an eukaryotic expressed E2 antigen analyzed under a native form i.e. visualized by an immunofluorescence assay (IFA). Such a detection assay has been previously used by Fournillier-Jacob et al., and shown to be particularly efficient for antibody detection (Fournillier-Jacob et al., 1996). Briefly, a recombinant plasmid, pCW18 E2, expressing HCV E2 amino acid sequence 371 to 746 from the prototype strain H (genotype 1a) was used to transfect CV-1 cells together with a helper SV40 mutant virus to generate the stock of recombinant virus expressing E2 (SVE2, Fournillier-Jacob et al., 1996, Wychowski et al., 1986). SVE2 virus was used to further infect CV-1 cells and immunofluorescence analysis were performed using sera from infected patients and supernatants from EBV-immortalized B cells as previously described (Fournillier-Jacob et al., 1996). Cells were fixed in methanol: acetone (3:7) prior to analysis. LCLs were further subcloned twice at 2 to 20 cells per well with 50×103 irradiated (2,500 rads) allogenic PBMCs. Two persistently positive clones derived from the two patients were obtained. Table 1 summarizes characteristics of the two patients and of the two lymphoid B-cell lines producing HMAbs, designated 503 and 108. Analysis of culture supernatants from the two clones revealed that both clones secreted IgG1 only. Supernatants from each clone were tested by IFA on CV-1 cells infected with the recombinant SVE2 virus and staining was revealed using specific secondary antibodies for human IgM, IgG or IgA (Byosis), IgG1, IgG2, IgG3 and IgG4 subclasses (Sigma Immuno Chemical Co.) and for λ and κ light chains (Dakopatts).

TABLE 1

Characteristics of patients and derived human anti-E2 monoclonal antibodies

| Patients | Genotype[a] | Viral load[b] Eq/ml × 10⁵ | Histological diagnosis | HMAbs | Isotype[c] |
|---|---|---|---|---|---|
| 1 | 4 | 5.2 | Mild Chronic Hepatitis | 503 | IgG1 λ |
| 2 | 1b | 21.8 | Cirrhosis | 108 | IgG1 λ |

[a]Analysis were made with samples derived from the day of patients' EBV-PBMC transformation as well as from two different time points during a two year follow-up. Results at the different time points and between the different assays were concordant.
[b]Quantified in serum with the Quantiplex bDNA assay (Quantiplex HCV RNA Assay, Chiron Diagnostics, Emeryville).
[c]Supernatants from each clone were tested by IFA on CV-1 infected cells with the recombinant SVE2 virus and staining was revealed using specific secondary antibodies for human IgM, IgG, IgA, IgG1-4 subclasses A protein A (Pharmacia) column was used for affinity purification of supernatant producing HMabs. The determination of antibody concentration in culture supernatants was performed by ELISA as previously described (Boyer et al., 1991). LCLs produced 2 to 5 μg of Ab/ml of conventional culture medium. Genotyping of patient 1 and 2 infecting viruses was at time of PBMC immortalization and on two times within the past two years prior to the immortalization using two different assays. Both assays gave concordant results and indicated that patient 1 was infected by a genotype 4 isolate while patient 2 was infected by a genotype 1 b isolate. As commercially available HCV genotyping assays may be lacking specificity and in order to exclude the possibility of dual infection, we further confirmed the above results by the analysis of PCR-derived sequences mapping within the 5'non-coding region of the HCV genome. Nucleotide sequences derived from cloned quasispecies was compared to published databases (Bukh et al., 1992) and the results confirmed those obtained with the commercial genotyping assays i.e. that both patients were infected with a single viral type. FIG. 1 illustrates the staining of SVE2 infected CV-1 cells observed in the IFA using the patients' sera (A and B) or the purified monoclonal antibodies (C and D). The reactivity was localized in the cytoplasm with a predominant perinuclear distribution.

EXAMPLE 2

Immunological Characteristics of the HMabs

Different approaches were used to characterize the immune reactivity of the produced antibodies. Western blot analysis using denaturing conditions and protein preparations containing subtype 1a or 1b derived E2 proteins (Nakano et al., 1997) were performed using the original patients' sera, supernatants from the LCLs as well as purified antibodies. For Western blotting analysis, baculovirus expressed E2 proteins from a genotype 1a and 1b sequence were used as previously described (Nakano et al., 1997). Patients' sera (1:50), supernatants from the two clones as well as purified HMabs (tested at a concentration as high as 10 µg/ml) were used. Epitope mapping using patient's sera as well as purified antibodies was performed using a panoply of synthetic peptides covering the entire E2 open reading frame as previously described (Courtesy A. M. Prince, Wang et al., 1996). The synthetic peptides were mostly 12-mer with 6 aa overlap between successive peptides, corresponding to the sequences of HCV-H strain (genotype 1a) E2 protein. There were a total of 57 peptides for E2 (aa 384-727), all of which were synthesized by AnaSpec.

While sera of both HCV infected patients reacted with the E2 1a and 1b derived proteins, none of the culture supernatants or purified HMAbs gave a positive signal, even when tested at concentrations as high as 10. µg/ml. No reactivity could either be observed when culture supernatants or purified antibodies were tested in a peptide scanning ELISA using a panel of synthetic peptides covering a E2 1a sequence.

As the above observations suggested that the recognized determinants may be of non-linear nature, immune reactivity of the different samples was analyzed in IF assays. Cells were transfected with a panoply of plasmids expressing different domains of E2 (see FIG. 2) in order to try and identify restricted determinant sequences The two HMabs obtained were evaluated for reactivity by IFA on LTK cells transfected by a panoply of vectors expressing truncated domains of the E2 protein (see FIG. 2). E2 sequences were cloned directly under the CMV promoter of the pcDNA3 plasmid (Promega) for plasmids pCIE2 and pCIE2t or expressed as fusion proteins with the hepatitis B virus surface antigens for plasmids pS2S.E2A-E using standard techniques and as previously described (Sambrook et al., 1989, Nakano et al., 1997). All DNA preparations were generated using Qiagen purification columns (Qiagen) according to the manufacturer's instructions. LTK cells were transfected using 1.0 µg of DNA in presence of Lipofectamine (Gibco BRL). The immune-reactivity of cell supernatants and of purified HMAbs were tested by IFA at 48 hours post infection as previously described (Major et al., 1995). Positive control included the use of a reactive hyperimmune serum generated from mice immunized by the direct injection of the plasmid pCIE2t (Nakano et al., 1997). Negative controls included the use of uninfected LTK cells as well as CV-1 cells infected with a recombinant SV40 virus expressing E1 (Fournillier-Jacob et al., 1996).

TABLE 2

Immune reactivity of patients's sera and of purified monoclonal antibodies (HMAbs) against truncated domains of E2

| | | HCV constructs[a] | | | | | | | |
|---|---|---|---|---|---|---|---|---|---|
| | | A | B | C | D | E | pCIE2α | pCIE2t | pcDNA3 |
| Patient 1[b] | serum | + | − | + | − | − | + | + | − |
| | HMAb 503 | − | − | − | − | − | − | + | − |
| Patient 2[c] | serum | − | − | − | − | − | − | + | − |
| | HMAb 108 | − | − | − | − | − | − | + | − |
| Mouse polyclonal Ab[d] | | + | + | + | + | + | + | + | − |

[a]LTK cells were transiently transfected with the indicated plasmids and IFA performed 48 hrs later as described in Major et al., (Major et al., 1995). The pS2.SE2A-E plasmids are according to Nakano et al., (Nakano et al., 1997). The pcDNA3 plasmid (Promega) was used as a negative control.
[b]Patients' sera were tested at 1/20 dilution; supernatants of LCLs or purified HMAbs were used at a concentration up o 10 µg/ml in at least two independently performed experiments.
[c]The efficiency of transfection and proper expression of the plasmids was evaluated in all cases using a reactive hyperimmune serum obtained from mice immunized by direct injection of the plasmid pCIE2t (Nakano et al., 1997).

Results of the IF studies are summarized in Table 2. Serum of patient 1 recognized multiple determinants mapping within the sequences expressed from various E2-expressing plasmids. In contrast, the HMAb 503 derived from this patient recognized only the near full-length expressed form of E2 (encoded by plasmid pCIE2t) but none of the smaller expressed forms of the antigen. For patient 2, the serum as well as the derived 108 antibody reacted only against the largest expressed form of E2. Thus, using this approach it was not possible to identify restricted determinant sequences recognized by either of the purified antibodies.

All the above experiments involved a subtype 1a derived antigen. It was evaluated the capacity of the purified monoclonal antibodies to, in addition, recognize a subtype 1 b derived E2 as a way to evaluate their cross-reactive potential. Reactivity of the HMAbs was tested by immunoprecipitation using cells infected with a recombinant Sindbis virus, Sinrep/HCV-BK1-1207, expressing such an antigen. Both antibodies were capable of recognizing the antigen as shown by the observation of strong, specific signals.

Taken together with the above results, these data suggest that the HMAbs are capable to recognize determinants specific of at least two different E2 subtype (1a and 1b) derived antigens. In addition, they strongly suggest that the antibodies are likely to recognize conformation-dependent determinants.

EXAMPLE 3

Immunoprecipitation Studies

The absence of reactivity of the HMAbs in western blotting and by IFA on LTK cells transfected by a panel of vectors expressing different truncated parts of E2 suggests that the Abs recognize conformation-dependent epitope(s). Therefore, it was further evaluated the recognition of E2 by the HMAbs in pulse chase experiments. In addition, as previous reports have suggested that E1 and E2 interact to form complexes which have been proposed to be functional subunits incorporated in the virion particles (Deleersnyder et al., 1997), the ability of the HMAbs to recognize such complexes was also evaluated. These E1E2 complexes are noncovalently associated or stabilized by intramolecular disulfide bonds forming E1 E2 aggregates.

Covalently associated E1E2 complexes have also been reported that are not believed to be part of the functional subunits of the viral particles (Dubuisson et al., 1994, Grakaoui et al., 1993, Ralston et al., 1993). For the purpose of the present invention, different recombinant viruses were used. These included: 1) a recombinant vaccinia virus vTF7.3 expressing the T7 DNA-dependent RNA polymerase (Fuerst et al., 1986), 2) a panoply of recombinant vaccinia viruses expressing HCV-H amino acid sequences, vHCV 170-809, vHCV 371-809, vHCV 1-1488 and vHCV 370-661 (Grakoui et al., 1993, Michalak et al., 1997, Fournillier-Jacob et al., 1996, Major et al., 1995) and 3) a recombinant Sindbis virus (Sinrep/HCV-BK1-1207) expressing the structural proteins of a genotype 1b strain, the BK strain (Dubuisson et al., 1994). Viral stocks were generated in CV-1 monolayers (for the vaccinia viruses) or in BHK-21 cells (for the Sindbis virus) as described (Dubuisson et al., 1994, Bredenbdeeck et al., 1993). Cells were infected and metabolically labeled with 35S-translabel (ICN) as previously described (Dubuisson et al., 1994, Dubuisson and Rice, 1996). Cells were lysed with 0.5% NP-40 in 10 mM Tris-HCl (ph 7.5), 150 mM NaCl, and 2 mM EDTA. Twenty mM iodoacetamide was included in the lysis buffer for experiments in which disulfide bond formation was assayed. Immunoprecipitations were carried out as described (Dubuisson et al., 1994, Dubuisson and Rice, 1996). For quantitative experiments, autoradiographs were analyzed by densitometry.

3.1 The HMAbs Recognize an Early Folded Domain of E

Immunoprecipitations were performed to characterize the proteins recognized by these HMAbs (FIG. 3). Murine anti-E2 MAbs directed at conformation-independent (MAb A 11) or conformation-dependent (MAb H2) epitopes were used for comparison (Dubuisson et al., 1994, Deleersnyder et al., 1997). Under reducing conditions, HMAbs 108 and 503 did not precipitate the E2 protein during the pulse, but after 30 min of chase a band corresponding to E2 started to be detected with an increased intensity after 60 min (FIG. 3, Reducing HMAbs 108 and 503). This is in contrast with results obtained using the murine MAb A 11 directed at a conformation-independent epitope (FIG. 3, Reducing, MAb A11). As previously observed with this latter antibody, heterogeneous E2 related products were detected during the pulse probably as a consequence of a translational pause during the synthesis of the NS2 region in the E2-NS2 precursor (Dubuisson et al., 1996). For the Mab A11, the intensity of the E2-NS2 precursor precipitated was very high after 30 min of chase and decreased with time whereas it was low and rather constant for the E2-NS2 protein precipitated by the HMAbs 108 and 503, indicating that E2 was mainly precipitated by the Abs after its cleavage from the E2-NS2 precursor. Comparison with immunoprecipitation performed with the conformation-dependent MAb H2 indicated a greater delay in the detection of E2 (FIG. 3, Reducing, Mab H2). These observations indicate that indeed the HMAbs recognize a conformation-dependent domain of E2 which appears early during the maturation process of the E2 protein. The estimated half-time of epitope formation for both HMAbs was around 15 min (data not shown).

3.2 The HMAbs can Precipitate Noncovalent E1 E2 Complexes

Additional pulse chase experiments were performed under non-reducing conditions and compared with those performed under reducing conditions (FIG. 3). While under reducing conditions, both HMAbs coprecipitated E1 indicating that they recognize E1 and E2 complexes, when immunoprecipitations were performed under non-reducing conditions which prevent the disulfide bonds stabilizing E1E2 complexes, slow migrating bands were also detected on the top of the gels. These latter observation suggests that the E1 E2 complexes precipitated consisted of noncovalently associated heterodimers and heterogeneous linked aggregates. As previously observed, for Mab H2 which has been shown capable to recognize a native form of E2, only bands corresponding to E1 and E2 were detected on the gel in that case (FIG. 3, non-reducing, H2, Deleersnyder et al., 1997). Under non-reducing conditions, the coprecipitation of the E1 monomeric form with HMAb 108 was poorer, with a specific band detected only after a long exposure time as compared with HMAb 503. Thus, both HMAbs recognize domain(s) of the E2 protein that appear folded early and would stay accessible as the protein adopts its final conformation as suggested by the coprecipitation of noncovalently associated E1 E2 complexes.

All together, the above data indicate that both HMAbs 108 and 503 recognize a conformation-dependent determinant (or determinants) and could precipitate E1 and E2 noncovalently associated complexes which are believed to exist on the virion particle.

EXAMPLE 4

Neutralization of E2 Binding onto Cells

The assay recently developed by Rosa et al., (Rosa et al., 1996) allows to evaluate, in a quantitative fashion, the ability of candidate antibodies to neutralize the binding of highly purified E2 (neutralizing of binding or NOB) onto cells susceptible to HCV infection. Both HMAbs were evaluated in this assay. The ability of the HMAbs was assessed to neutralize the binding (Neutralization of Binding or NOB) of E2 to MOLT 4 cells in the assay recently developed by Rosa et al. (Rosa et al., 1996). The assay was run in 96 U-bottom microplates. Briefly, twenty μl of recombinant CHO $E2_{384-715}$ proteins at 0.5 μg/ml was mixed with various dilution of anti-E2 HMAbs and control HMAbs (Rosa et al., 1996, Boyer et al., 1991). After incubation at 4° C. for 1 h, the mixture was added to MOLT-4 cells (105 cells per well). After washing, cells were subsequently incubated with 1/100 dilution of human serum with anti-E2 immunoglobulins which recognizes E2 bound to target cells. Cells were washed and incubated with fluoresceine isothiocianate-conjugated antiserum to IgG. Fluorescence was analyzed with a FACScan flow cytometer. Specific neutralization was calculated as follow: ((positive control MFI−experimental MFI )/(positive control MFI−negative control MFI))×100 where (MFI)=mean fluorescence intensity of the cell population which directly relates to the surface density of fluorescently labeled HCV proteins bound to the cells. MFI values of cells incubated with or without HCV proteins and with the HCV HMAbs or HCV-negative HMAbs or pre-immune sera (Rosa et al., 1996) are compared. The threshold of positivity is set for each experiment by flow cytometric analysis of cells without HCV proteins bound that have been incubated with antisera to HCV proteins and the fluorescein isothiocyanate-labeled second antibody. For competition binding analysis, antibodies were biotinylated as followed: 1 mg/ml of the antibodies in 0. 4 M phosphate buffer were incubated with N-N-dimethylformamide biotin at 2 mg/ml at 4° C. for 2 hrs and dialyzed extensively against PBS overnight. Testing of the NOB activity was performed using both antibodies, the competitor labeled antibody being used at 2.5 µg/ml.

Percent neutralization obtained at different concentrations of the antibodies are shown in FIG. 4. The results indicate that the HMAb 503 displayed NOB activity and that fifty percent neutralization of binding was achieved at a concentration of 0.03 µg/ml. No NOB activity could be detected for HMAb 108 at any of the concentration tested. Hence, the HMAb 503 that is capable of NOB activity is the first such antibody described to date. Interestingly, the fact that the producing clone (503) was derived from a genotype 4 infected patient while the assay used a genotype 1(a) derived antigen confirms the cross-reactive potential of this antibody. The data also suggest that antibodies with NOB-activity seem to be targeted at determinants conserved between different viral genotypes.

Competition experiments were performed to determine whether the two antibodies binds to similar or topographically distinct epitopes. The HMAb 108 did not prevent (i.e. did not compete) the detection of the neutralizing activity of the 503 Ab. These results strongly suggest that the HMAbs 108 and 503 recognize different epitopes on the E2 protein.

EXAMPLE 5

Prevention of HCV Infection in Liver Transplantation

The following describes a liver transplantation in the case of an infection with hepatitis C virus (HCV), whereby an antibody of the invention is administered in order to avoid a re-infection of the implanted organ.

Preparation of the patient: shaving of the whole body, clystering, taking blood (quantitatively determining HCV-RNA), decontamination of the intestine with the help of drugs.

Preparation of the donor (death of the brain certified, heart is still beating): taking blood (checking for antibodies against hepatitis B, C; HIV, cytomegalovirus), removal of the organ, conservation for the transport to the University of Wisconsin in a conservation medium (electrolyte solution rich in kalium, kept at a temperature of 4° C.) and transport to the patient. The patient is given general anesthesia+immunosuppression in the O.R. (approx. 1 g prednisolone+FK 506 or cyclosporine A+optionally azathriopine+optionally antithymocyte globulin); stomach is opened (laparotomy); a bypass is fixed between vena femoralis (ridge) and vena axillaris (axilla) in order to stabilize the blood circulation; the liver is removed from the surrounding tissue, afferent and efferent vessels are prepared (arteria hepaticae, vena portae, ductus choleductus, vena hepaticae) and the liver is mobilized (Pringel-Manöver). The vessels are clamped and the liver is removed.

At this stag the antibody is administered: 100-200 mg antibody+500 mg human serum albumin as a lyophilisate or as a concentrated solution are dissolved in 100 ml isotonic salt solution or in a 5% glucose solution and infused in the course of two hours. During the infusion the donor organ is placed into the patient's abdominal region. The vessels are anastomosed (sutured), and again a blood probe is taken (determination of HCV-RNA-titer). After the infusion has been terminated, the vessels are re-perfused and checked for closeness. If they are closed, the liver is placed in the abdominal region. One hour after the perfusion was started, a biopsy of the liver is taken and the abdomen is closed. The biopsy is immunohistochemically analyzed if the antibody has reached a target.

The patient is brought to the intensive care unit, kept under anaesthetic and artificially ventilated. Liver function, secondary hemorrhages, vascular occlusion, stage of the infection, antibody concentration as well as HCV-RNA-titer in the blood are closely monitored (normal course of the HCV-RNA-titer: after several days below demonstration level it increases after approx. one week).

Long-term course: In the first period of time 100 mg prednisolone per day are administered, the dose is decreased to 5 mg in the course of three month; prednisolone as well as individual doses of FK506 or cyclosporine are administered for the whole life, azathriopine and/or antithymocyte globulin only in the first four weeks. The therapeutic antibody will probably be renewed every six to eight weeks (infusion 100-200 mg); the HCV-RNA titer and the concentration of the antibody will be determined every four weeks. If there is known more about the antibody, the measurement will not be necessary anymore. Liver function, infections and possible rejection reactions (biopsy) are monitored for the whole life. Preexposure prophylaxis (partners of infected people; usually protection by the use of condoms if no pregnancy is desired): Every six to eight weeks bolus of 100-200 mg antibody intramuscularly (if sufficiently acceptable) or via infusion. Monitoring of the antibody concentration in the blood.

For postexposure prophylaxis (nurse who has stung herself with a needle etc.) blood is taken (HCV-RNA-titer is determined), before result is there, 100-200 mg antibody are given via infusion.

EXAMPLE 6

Cloning and Determination of Functional Immunoglobulin Variable Region Sequences of the Human Anti-HCV Antibody and Expression in CHO-cells Total RNA was prepared from the antibody producing EBV-transformed human B cell line according to Chomczynski (Analytical biochemistry 162 (1987) 156-159). Subsequently, cDNA was synthesized according to standard protocols (Sambrook, Cold Spring Harbour Laboratory Press 1989, second edition).

The DNA-regions that encode the lambda-light chain and the γ1-heavy chain Fd-segment (VH+CH1) of the human anti-HCV antibody were amplified by PCR using the oligonucleotide primer set listed in Table 3 and the cDNA synthesized from said human B cell line as template.

This primer set gives rise to a 5'- XhoI and a 3'- SpeI recognition site for the heavy chain Fd-fragment and to a 5'-SacI and a 3'- XbaI recognition site for the lambda light chain. For the PCR-amplification of the heavy chain Fd-encoding DNA-fragment five different 5'-VH-primers (VH1, 3,5,7, VH2, VH4, VH4B and VH6) were each combined with the 3'-VH primer CGd1; for the PCR-amplification of the lambda light chain fragment eight different 5'-VL primers (VL1-8) were each combined with the 3'-VL primer CL2.

The following PCR programm was used for amplification: Denaturation at 94° C. for 20 sec.; primer annealing at 52° C. for 50 sec. and primer extension at 72° C. for 60 sec. for 40 cycles, followed by a 10 min. final extension at 72° C.

PCRs were run on agarose gel and DNA bands of the appropriate size isolated. Each isolated DNA band was subsequently digested with the restriction enzymes Xho I and Spe I (in case of heavy chain fragments) or with Sac I and Xba I (in case of light chain fragments) and cloned into the plasmid vector Bluescript (Stratagene) that was either prepared by digestion with Xho I and Spe I or by cleavage with Sac I and Xba I.

Plasmid preparations of cloned heavy chain and light chain fragments were subsequently subjected to sequence analysis. Two sequences were selected that encode for functional immunoglobulin heavy chain and light chain variable regions (VH and VL), respectively; exactly one functional VH region and one functional VL region could thus be identified. Functional VL sequences and VH sequences are depicted in FIGS. 5 (SEQ ID NOS:1 and 2) and 6 (SEQ ID NOS:3 and 4). The amino acid sequence of the mature N-terminus was each completed by comparison with the corresponding germline sequences as provided by a Human V Gene Sequence databank, for example, available on the MRC Centre for Protein Engineering website.

Cloning and sequencing was carried out according to standard methods (Sambrook, Cold Spring Harbour Laboratory Press 1989, second edition). In order to clone VL- and VH-fragments that contain the original N-termini of heavy and light chain of the human anti-HCV antibody, the following experimental procedure was carried out:

The total RNA was reverse transcribed with the MMLV reverse transcriptase Superscript II (Gibco BRL, Eggenstein) according to standard protocols (Sambrook, Cold Spring Harbour Laboratory Press 1989, second edition). Specific priming of cDNA was carried out with the two oligonucleotides CGd1 (for the heavy chain) and CL2 (for the light chain).

The first strand of cDNA was then poly-G tailed using terminal transferase (Pharmacia, Freiburg) according to standard protocols. The tailed cDNA was PCR-amplified using a sense primer containing a poly-C stretch, based on the anchor primer sequence published by Gilliland, L. K. et al., (Tissue Antigens 47, 1-20, 1996) and designated 5'-AncTail (CGTCGATGAGCTCTAGAATTCCCCCCCCCCCCCD (SEQ ID NO:7). This anchor primer was combined with an antisense primer, specific for the nucleotide sequence encoding the C-terminus of the lambda light chain constant region (CL2) or that of the IgG1-CH1 heavy chain domain (CGd1), respectively.

The PCR was carried out as follows: Primary denaturation: 94° C. for 4 min.; 30 cycles of amplification: 93° C. for 30 sec.; 55° C. for 30 sec.; 72° C. for 30 sec.; terminal elongation: 72° C. for 3 min. Each of these primers contain a restriction enzyme cleavage site (5'-AncTail: EcoRI; CL2: XbaI; CGd1: SpeI) which allows cloning of the corresponding PCR-fragments into a plasmid vector digested with EcoRI/XbaI or EcoRI/SpeI, respectively; for this purpose the bluescript KS+ plasmid vector (Genebank Accession No X52327) was used, since it also allows easy sequence analysis of the resulting inserts by using common sequencing primers. Several clones of heavy and light chain fragments proved to have identical sequences, respectively and could be identified to encode either functional VL- or VH-regions. The VH-sequence proved to be identical with that cloned by the above mentioned method. The amino acid sequence of VL (SEQ ID NO: 6) turned out to carry one amino acid replacement at position 2 of the mature N-terminus, compared to the VL-sequence obtained by the above mentioned method.

The complete lambda light chain including the native leader peptide, was cloned according to standard procedures via PCR into the mammalian expression vector pEF-ADA (see PCT/EP98/02180). VH was also cloned according to standard procedures via PCR into the genomic context of a human γ1-heavy chain in the mammalian expression vector pEF-DHFR as described in PCT/EP98/02180.

Expression of the complete human IgG1λ-antibody was performed by stable transfection of CHO-cells and subsequent gene amplification as described (PCT/EP98/02180).

Purification of the antibody from cell culture supernatant was carried out by Protein A affinity chromatography as described in PCT/EP98/02180.

TABLE 3

List of primers

5'-VH primer set:

| | |
|---|---|
| VH1,3,5,7: | AGGTGCAGCTGCTCGAGTCTGG (SEQ ID NO:8) |
| VH2: | CAG(AG)TCACCTTGCTCGAGTCTGG (SEQ ID NO:9) |
| VH4: | CAGGTGCAGCTGCTCGAGTCGGG (SEQ ID NO:10) |
| VH4B: | CAGGTGCAGCTACTCGAGTGGGG (SEQ ID NO:11) |
| VH6: | CAGGTACAGCTGCTCGAGTCAGG (SEQ ID NO:12) |

3'-VH primer:

| | |
|---|---|
| CGd1 | GCATGTACTAGTTTTGTCACAAGATTTGG (SEQ ID NO:13) |

5' VL primer set:

| | |
|---|---|
| VL1: | AATTTTGAGCTCACTCAGCCCCAC (SEQ ID NO:14) |
| VL2: | TCTGCCGAGCTCCAGCCTGCCTCCGTG (SEQ ID NO:15) |
| VL3: | TCTGTGGAGCTCCAGCCGCCCTCAGTG (SEQ ID NO:16) |
| VL4: | TCTGAAGAGCTCCAGGACCCTGTTGTGTCTGTG (SEQ ID NO:17) |
| VL5: | CAGTCTGAGCTCACGCAGCCGCCC (SEQ ID NO:18) |
| VL6: | CAGACTGAGCTCACTCAGGAGCCC (SEQ ID NO:19) |
| VL7: | CAGGTTGAGCTCACTCAACCGCCC (SEQ ID NO:20) |
| VL8: | CAGGCTGAGCTCACTCAGCCGTCTTCC (SEQ ID NO:21) |

3' VL primer:

| | |
|---|---|
| CL2: | CGCCGTCTAGAATTATGAACATTCTGTAGG (SEQ ID NO:22) |

REFERENCES

Abrignani, Springer Semin. Immunopathol. 19 (1997), 47-55.
Akatsuka, Hepatology 18 (1993), 503-510.
Bhattacherjee, J. Gen. Virol. 76 (1995), 1737-1748.
Bergeron, Trends Biochem. Sci. 19 (1994), 124-129.
Boyer, Clin. exp. Immunol. 83 (1991), 452-459.
Bredenbeek, J. Virol. 67 (1993), 6439-6446.
Bukh, Proc. Natl. Acad. Sci. USA. 89 (1992), 4942-4946.
Cerino, J. Immunol. 147 (1991), 2692-2696.
Cerino, J. Immunol. 151 (1993), 7005-7015.
Chan, J. Gen. Virol. 77 (1996), 2531-2539.
Chien, Lancet 342 (1993), 933.
Choo, Science 244 (1989), 359-362.

Choo, Proc. Natl. Acad. Sci. USA. 91 (1994), 1294-1298.
Conley, J. Virol. 70 (1996), 6751-6758.
Deleersnyder, J. Virol. 71 (1997), 697-704.
Desgranges, Lancet, 8591 (1988), 935-936.
Dubuisson, J. Virol. 68 (1994), 6147-6160.
Dubuisson, J. Virol. 70 (1996), 778-786.
Emini, Nature 355 (1992), 728-730.
Farci, Proc. Natl. Acad. Sci. USA. 91 (1994), 7792-7796.
Farci, Proc. Natl. Acad. Sci. USA. 93 (1996), 15394-15399.
Fournillier-Jacob, J. Med. Virol. 50 (1996), 159-167.
Fournillier-Jacob, J. Gen. Virol. 77 (1996), 1055-1064.
Fouts, J. Virol. 71 (1997), 2779-2785.
Francki, Arch. Virol. 2 (1991), 223-233.
Fuerst, Proc. Natl. Acad. Sci. USA. 93 (1986), 8122-8126.
Gakoui, J. Virol. 67 (1993), 1385-1395.
Hsu, Hepatology 17 (1993), 763-771.
Fuerst, Proc. Natl. Acad. Sci. USA. 83 (1986), 8122-8126.
Lesniewski, J. Med. Virol. 45 (1995), 415-422.
Lanford, Virology 197 (1993), 225-235.
Major, J. Virol. 69 (1995), 5798-5805.
Michalak, J. Gen. Virol. 78 (1997), 2299-2306.
Miller, Proc. Natl. Acad. Sci. USA. 87 (1990), 2057-2061.
Miyamura, Trends Microbiol. 1 (1993), 229-231.
Mondelli, J. Virol. 68 (1994), 4829-4836.
Nakano, J. Virol. 71(1997), 7101-7109.
Putkonen, Nature 352 (1991), 436-438.
Ralston, J. Virol. 67 (1993), 6753-6761.
Rice, Fields Virology, Third edition. Raven Press, New York (1996).
Rosa, Proc. Natl. Acad. Sci. USA. 93 (1996), 1759-1763.
Saito, Proc. Natl. Acad. Sci. USA. 87 (1990), 6547-6549.
Sambrook, Molecular cloning: a laboratory manual, 2nd ed. Cold Spring Harbor Laboratory Press. Cold Spring Harbor, New York (1989).
Seigneurin, Science 221 (1983), 173-175.
Selby, J. Gen. Virol. 74 (1993), 1103-1113.
Shimizu, J. Virol. 68 (1994), 1494-1500.
Shimizu Virology 223 (1996), 409-412.
Weiner, Virology 180 (1991), 842-848.
Wang, J. Inf. Dis. 173 (1996), 808-821.
Wychowski, EMBO J. 5 (1986), 2569-2576.
Zibert, Virology 208 (1995), 653-661.
Zibert, Hepatology 25 (1997), 1245-1249.

The invention claimed is:

1. An isolated antibody, wherein said antibody specifically recognizeds the same conformation-dependent epitope of Hepatitis C Virus (HCV) E2 present on HCV genotypes 1a, 1b, 2, 3a and 4 as that bound by an antibody comprising the complementarity determining regions (CDR) of SEQ ID NO: 2 and the CDRs of SEQ ID NO: 4, and precipitates covalently or non-covalently associated E2/E1 complexes.

2. The isolated antibody of claim 1, wherein said antibody is a monoclonal antibody, a polyclonal antibody, a chimeric antibody, a humanized antibody, a synthetic antibody, or an antigen-binding antibody fragment.

3. The isolated antibody of claim 2, wherein said antibody is a monoclonal antibody.

4. The isolated antibody of claim 1, wherein said antibody comprises the VL amino acid sequence SEQ ID NO: 2.

5. The isolated antibody of claim 3, wherein said antibody is a human monoclonal antibody.

* * * * *